United States Patent [19]

Akita et al.

[11] 4,078,138

[45] Mar. 7, 1978

[54] 3'-EPI-4'DEOXYKANAMYCIN B

[75] Inventors: Eiichi Akita, Kamakura; Yukio Horiuchi, Yokohama; Takeo Miyazawa, Yokohama; Toshio Yoneta, Yokohama; Sumio Umezawa; Hamao Umezawa, both of Tokyo, all of Japan

[73] Assignee: Meiji Seika Kaisha, Ltd., Tokyo, Japan

[21] Appl. No.: 638,045

[22] Filed: Dec. 5, 1975

[30] Foreign Application Priority Data

Dec. 11, 1974 Japan .................................. 49-141498

[51] Int. Cl.$^2$ ............................................ C07H 15/22
[52] U.S. Cl. ...................................... 536/10; 424/180; 536/17
[58] Field of Search .................... 260/210 AB, 210 K; 536/17, 10

[56] References Cited

U.S. PATENT DOCUMENTS

| | | | |
|---|---|---|---|
| 3,920,628 | 11/1975 | Daniels et al. | 260/210 AB |
| 3,929,762 | 12/1975 | Umezawa et al. | 260/210 AB |

OTHER PUBLICATIONS

Baker et al., "Jour. Amer. Chem. Soc." vol. 77, 1955, pp. 7–9.

*Primary Examiner*—Johnnie R. Brown
*Attorney, Agent, or Firm*—Haight & Huard

[57] ABSTRACT

3',4'-α-Epoxyneamine and its related aminoglycosidic antibiotic derivatives containing 3',4'-α-epoxyneamine moiety in the molecule thereof are now provided, which may be in the form of their amino-protected and partially hydroxyl-protected product and which are useful as intermediates for use in the synthetic production of therapeutically valuable 3'-deoxy derivatives of aminoglycosidic antibiotics.

1 Claim, No Drawings

3'-EPI-4'DEOXYKANAMYCIN B

This invention relates to a process for the production of 3',4'-epoxyneamine and its related aminoglycosidic antibiotic derivatives containing the 3',4'-α-epoxyneamine moiety in the molecule thereof. This invention also relates to 3',4'-α-epoxyneamine and its related aminoglycosidic antibiotic derivatives containing 3',4'-α-epoxyneamine moiety in the molecule thereof as new and useful intermediate compounds. As the aminoglycosidic antibiotics containing a neamine moiety in the molecule thereof are known neamine (that is, neomycin A), neomycin B, neomycin C, ribostamycin (known also as vistamycin), xylostatin, butirosin A, butirosin B and kanamycin B. From Belgian Pat. No. 808,393, DT-OS 2,361,159 and Japanese patent pre-publication No. 80038/74, it is known that some aminoglycosidic antibiotics containing the neamine moiety in the molecule thereof may be converted into their 3'-O-sulfonyl derivatives by selective 3'-O-sulfonylation while partly or wholly protecting the functional amino groups and with or without protecting the functional hydroxyl groups other than the 3'-hydroxyl group of said aminoglycosidic antibiotics, and that these 3'-O-sulfonyl derivatives of the aminoglycosidic antibiotics may then be converted into therapeutically useful 3'-deoxy derivatives of aminoglycosidic antibiotics by reacting said 3'-O-sulfonyl derivative with an alkali metal bromide or iodide to give a corresponding 3'-bromo or 3'-iodo derivative, followed by catalytic hydrogenation of the 3'-bromo or 3'-iodo compound.

As shown in a co-pending U.S.A. patent application Ser. No. 598,379; British patent application No. 30659/75; German patent application No. P 25 33 985.9; and French patent application No. 75.24592 of the same assignee, we have proposed a new process for the production of therapeutically useful 3'-deoxy derivatives of particular aminoglycosidic antibiotics selected from the group consisting of neamine, 6'-N-alkylneamine, kanamycin B, 6'-N-alkylkanamycin B, ribostamycin and 6'-N-alkylribostamycin, comprising the steps of selective 3'-O-sulfonylation of a hydroxyl-protected and amino-protected derivative of these particular aminoglycosidic antibiotics to prepare the corresponding 3'-O-sulfonyl derivative, and subsequent treatment of the 3'-O-sulfonyl derivative with an alkali metal hydroxide or alkoxide in a lower alkanol to effect the epoxidation between the 4'-hydroxyl group and the carbon atom substituted by the 3'-sulfonic ester group and thereby to give the corresponding 3',4'-α-epoxy derivative, followed by the removal of the remaining protective groups. At that time, it was found that the epoxidation takes place easily in a high yield when the 3'-O-sulfonyl derivative of the above-mentioned particular aminoglycosidic antibiotics is treated with an alkali metal hydroxide or alkoxide in a lower alkanol. The above epoxidation may take place by treating a hydroxyl-protected and amino-protected 3'-O-sulfonyl derivative of another aminoglycosidic antibiotics with an alkali, in general. Thus, the above epoxidation may generally be applied to a hydroxyl-protected and amino-protected 3'-O-sulfonyl derivative of neamine and of an aminoglycosidic antibiotic containing the neamine moiety in the molecule thereof.

An object of this invention is to provide such a 3',4'-α-epoxy derivative of aminoglycosidic antibiotic which is a new intermediate compound useful for the semisynthetic production of therapeutically valuable 3'-deoxy derivatives of aminoglycosidic antibiotics. The other object of this invention is to provide a process by which the 3',4'-α-epoxy derivative of aminoglycosidic antibiotic can be prepared in an efficient and facile way. Other objects of this invention will be clear from the following description.

According to an aspect of this invention, therefore, there is provided a process for the production of an aminoglycosidic antibiotic derivative containing a 3',4'-α-epoxyneamine moiety in its molecule, including 3',4'-α-epoxyneamine itself, and an amino-protected and optionally hydroxyl-protected derivative thereof, which comprises treating with an alkali such a derivative of an aminoglycosidic antibiotic containing a 3'-O-sulfonylneamine moiety in its molecule which has been derived from the 3'-O-sulfonylation of the parent aminoglycosidic antibiotic containing the neamine moiety in its molecule and of which the amino and hydroxyl functions have partly or wholly been protected or are unprotected, to effect the epoxidation between the 4'-hydroxyl group (either unprotected or acylated with a hydroxyl-protecting group of an alkanoyl type or with benzoyl group) and the carbon atom to which is attached the 3'-sulfonic ester group, and then, if desired, removing the remaining amino-protecting group and hydroxyl-protecting group from the resultant 3',4'-α-epoxidation product.

As examples of the parent aminoglycosidic antibiotic containing the neamine moiety in the molecule thereof which is employed as the initial material to prepare the 3'-O-sulfonyl derivative therefrom, there may be mentioned neamine (i.e. neomycin A), neomycin B, neomycin C, ribostamycin, xylostatin, butirosin A, butirosin B, kanamycin B; 6'-N-alkyl derivatives of the aforesaid aminoglycosidic antibiotics; 1-N-(α-hydroxy-ω-aminoalkanoyl) derivatives of the aforesaid aminoglycosidic antibiotics; 6'-N-alkyl-(α-hydroxy-ω-aminoalkanoyl) derivatives of the aforesaid aminoglycosidic antibiotics; and a variety of the other aminoglycosidic antibiotics containing the neamine moiety in the molecule thereof.

The 3'-O-sulfonyl derivative of an aminoglycosidic antibiotic containing the 3'-O-sulfonylneamine moiety in the molecule thereof which is employed as the starting material in the process of this invention may be prepared from the above-mentioned parent aminoglycosidic antibiotic containing the neamine moiety in the molecule thereof by selectively 3'-O-sulfonylating the latter with an alkylsulfonylating agent, benzylsulfonylating agent or an arylsulfonylating agent with or without protecting all or parts of the functional amino groups and hydroxyl groups. The selective 3'-O-sulfonylation may conveniently be carried out at a temperature of up to 50° C in an inert organic solvent such as dimethylformamide and is described in detail in the aforesaid Belgian Pat. No. 808,393 and DT-OS No. 2,361,159. Suitable examples of sulfonylating agents which are useful in this invention include methanesulfonic chloride or bromide, ethanesulfonic chloride or bromide, benzylsulfonic chloride or bromide, tosyl chloride or bromide and benzenesulfonic chloride or bromide.

As typical examples of the 3'-O-sulfonyl derivative of an aminoglycosidic antibiotic containing the 3'-O-sulfonylneamine moiety in its molecule which is prepared in the above-mentioned way, there may be mentioned 3'-O-sulfonyl derivatives of neamine, a 6'-N-alkylneamine, a 1-N-(α-hydroxy-ω-aminoalkanoyl)neamine, a 6'-N-alkyl-1-N-(α-hydroxy-ω-aminoalkanoyl)neamine, ribostamycin, a 6'-N-alkylribostamycin, a 1-N-(α-hydroxy-ω-aminoalkanoyl)ribostamycin, a 6'-N-alkyl-1-N-(α-hydroxy-ω-aminoalkanoyl)ribostamycin, xylostatin, a 6'-N-alkylxylostatin, a 1-N-(α-hydroxy-ω-aminoalkanoyl) xylostatin, a 6'-N-alkyl-1-N-(α-hydroxy-ω-aminoalkanoyl) xylostatin, neomycin B, a 6'-N-alkylneomycin B, a 1-N-(α-hydroxy-ω-aminoalkanoyl)neomycin B, a 6'-N-alkyl-1-N-(α-hydroxy-ω-aminoalkanoyl)neomycin B, neomycin C, a 6'-N-alkylneomycin C, a 1-N-(α-hydroxy-ω-aminoalkanoyl)neomycin C, a 6'-N-alkyl-1-N-(α-hydroxy-ω-aminoalkanoyl)neomycin C, kanamycin B, a 6'-N-alkylkanamycin B, a 1-N-(α-hydroxy-ω-aminoalkanoyl) kanamycin B and a 6'-N-alkyl-1-N-(α-hydroxy-ω-aminoalkanoyl)kanamycin B, respectively.

According to an embodiment of this invention, as the starting 3'-O-sulfonyl derivative of aminoglycosidic antibiotic for the present process there is used a 3'-O-sulfonyl compound represented by the following general formula (I):

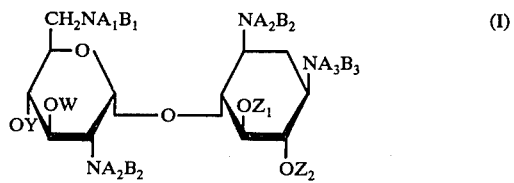

wherein either $A_1$ and $B_1$ are each a hydrogen atom, or $A_1$ is an alkyl group and particularly a lower alkyl group of 1-4 carbon atoms and $B_1$ is a hydrogen atom, or $A_1$ is a hydrogen atom and $B_1$ is a known mono-valent amino-protecting group, for example, an alkoxycarbonyl group of 2-7 carbon atoms such as methoxycarbonyl, ethoxycarbonyl and t-butoxycarbonyl, an aryloxycarbonyl group such as phenoxycarbonyl, an arylmethoxycarbonyl group such as benzyloxycarbonyl or an alkanoyl group such as acetyl and an aroyl group such as benzoyl, or $A_1$ and $B_1$ taken together form a known di-valent amino-protecting group such as phthaloyl; either $A_2$ and $B_2$ are each a hydrogen atom, or $A_2$ is a hydrogen atom and $B_2$ is a known mono-valent amino-protecting group such as those mentioned above, or $A_2$ and $B_2$ taken together form a known di-valent amino-protecting group such as phthaloyl; either $A_3$ and $B_3$ are each a hydrogen atom, or $A_3$ is a hydrogen atom and $B_3$ is a known mono-valent amino-protecting group such as those mentioned above, or $A_3$ is a hydrogen atom and $B_3$ is an α-hydroxy-ω-aminoalkanoyl group (such as isoseryl and α-hydroxyl-γ-butyryl) of which the amino functions and hydroxyl functions may wholly or partly be protected or are unprotected, or $A_3$ and $B_3$ taken together form a known di-valent amino-protecting group such as phthaloyl; W is an alkylsulfonyl group, particularly an alkylsulfonyl group of 1-4 carbon atoms such as mesyl, or benzylsulfonyl group or an arylsulfonyl group such as benzenesulfonyl and tosyl; Y is a hydrogen atom or a known hydroxyl-protecting group of the acyl type, particularly a known hydroxyl-protecting group of an alkanoyl type such as acetyl and an aroyl group such as benzoyl; either $Z_1$ and $Z_2$ are each a hydrogen atom; or $Z_1$ and $Z_2$ taken together form a known di-valent hydroxyl-protecting group, for example, an akylidene group such as isopropylidene and cyclohexylidene as well as an arylidene group such as benzylidene when the whole molecule of the 3'-O-sulfonyl compound of the above formula (I) forms the 3'-O-sulfonyl derivative of neamine, 6'-N-alkylneamine, 1-N-(α-hydroxy-ω-aminoalkanoyl)neamine or 6'-N-alkyl-1-N-(α-hydroxy-ω-aminoalkanoyl)neamine; or $Z_1$ is a β-D-ribofuranosyl group of which the hydroxyl functions may partly or wholly be protected or unprotected, and $Z_2$ is a hydrogen atom or a known mono-valent hydroxyl-protecting group, for example, of the acyl type, particularly an alkanoyl group such as acetyl, an aroyl group such as benzoyl and an arylmethyl group such as benzyl when the whole molecule of the 3'-O-sulfonyl compound of the above formula (I) forms the 3'-O-sulfonyl derivative of ribostamycin, 6'-N-alkylribostamycin, 1-N-(α-hydroxy-ω-aminoalkanoyl)ribostamycin or 6'-N-alkyl-1-N-(α-hydroxy-ω-aminoalkanoyl)ribostamycin; or $Z_1$ is a β-D-xylofuranosyl group of which the hydroxyl functions may be protected or unprotected, and $Z_2$ is a hydrogen atom or a known mono-valent hydroxyl-protecting group such as those mentioned above when the whole molecule of the 3'-O-sulfonyl compound of the above formula (I) forms the 3'-O-sulfonyl derivative of xylostatin, 6'N-alkylxylostatin, 1-N-(α-hydroxy-ω-aminoalkanoyl)xylostatin or 6'-N-alkyl-1-N-(α-hydroxy-ω-aminoalkanoyl)xylostatin; or $Z_1$ is a 3''-O-(α-L-2''',6'''-diaminodideoxyidopyranosyl)-β-D-ribofuranosyl group of which the hydroxyl and amino functions may partly or wholly be protected, and $Z_2$ is a hydrogen atom or a known mono-valent hydroxyl-protecting group when the whole molecule of the 3'-O-sulfonyl compound of the formula (I) forms the 3'-O-sulfonyl derivative of neomycin B, 6'-N-alkylneomycin B, 1-N-(α-hydroxy-ω-aminoalkanoyl)neomycin B or 6'-N-alkyl-1-N-(α-hydroxy-ω-aminoalkanoyl)neomycin B; or $Z_1$ is a 3''-O-(α-L-2''',6'''-diaminodideoxyglucopyranosyl)-β-D-ribofuranosyl group of which the hydroxyl and amino functions may partly or wholly be protected and $Z_2$ is a hydrogen atom or a known mono-valent hydroxyl-protecting group such as those mentioned above when the whole molecule of the 3'-O-sulfonyl compound of the formula (I) forms the 3'-O-sulfonyl derivative of neomycin C, 6'-N-alkylneomycin C, 1-N-(α-hydroxy-ω-aminoalkanoyl)neomycin C or 6'-N-alkyl-1-N-(α-hydroxy-ω-aminoalkanoyl)neomycin C; or $Z_1$ is a hydrogen atom and $Z_2$ is a 3''-aminodeoxy-α-D-glucopyranosyl group of which the amino and hydroxyl functions may partly or wholly be protected when the whole molecule of the 340 -O-sulfonyl compound of the above formula (I) forms the 3'-O-sulfonyl derivative of kanamycin B, 6'-N-alkylkanamycin B, 1-N-(α-hydroxy-ω-aminoalkanoyl)kanamycin B or 6'-N-alkyl-1-N-(α-hydroxy-ω-aminoalkanoyl)kanamycin B.

When the 3'-O-sulfonyl compound of the formula (I) is subjected to the epoxidation by treating with an alkali according to the process of this invention, there is produced as a new compound a 3',4'-α-epoxyneamine derivative represented by the following general formula (II):

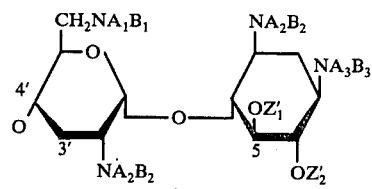

wherein either $A_1$ and $B_1$ are each a hydrogen atom, or $A_1$ is an alkyl group of 1–4 carbon atoms and $B_1$ is a hydrogen atom, or $A_1$ is a hydrogen atom and $B_1$ is a known mono-valent amino-protecting group, or $A_1$ and $B_1$ taken together form a known di-valent amino-protecting group; either $A_2$ and $B_2$ are each a hydrogen atom, or $A_2$ is a hydrogen atom and $B_2$ is a known mono-valent amino-protecting group, or $A_2$ and $B_2$ taken together form a known di-valent amino-protecting group; either $A_3$ and $B_3$ are each a hydrogen atom, or $A_3$ is a hydrogen atom and $B_3$ is a known mono-valent amino-protecting group, or $A_3$ is a hydrogen atom and $B_3$ is an α-hydroxy-ω-aminoalkanoyl group of which the amino function may be protected, or $A_3$ and $B_3$ taken together form a known di-valent amino-protecting group; either $Z_1'$ and $Z_2'$ are each a hydrogen atom, or $Z_1'$ and $Z_2'$ taken together form a known di-valent hydroxyl-protecting group when the whole molecule of the compound of the above formula (II) forms the 3′,4′-α-epoxy derivative of neamine, 6′-N-alkylneamine, 1-N-(α-hydroxy-ω-aminoalkanoyl) neamine or 6′-N-alkyl-1-N-(α-hydroxy-ω-aminoalkanoyl) neamine; or $Z_1'$ is a β-D-ribofuranosyl group of which the hydroxyl function may be protected, and $Z_2'$ is a hydrogen atom or a known mono-valent hydroxyl-protecting group when the whole molecule of the compound of the formula (II) forms the 3′,4′-α-epoxy derivative of ribostamycin, 6′-N-alkylribostamycin, 1-N-(α-hydroxy-ω-aminoalkanoyl)ribostamycin or 6′-N-alkyl-1-N-(α-hydroxy-ω-aminoalkanoyl)ribostamycin; or $Z_1'$ is a β-D-xylofuranosyl group of which the hydroxyl functions may be protected, and $Z_2'$ is a hydrogen atom or a known mono-valent hydroxyl-protecting group when the whole molecule of the compound of the formula (II) forms the 3′,4′-α-epoxy derivative of xylostatin, 6′-N-alkylxylostatin, 1-N-(α-hydroxy-ω-aminoalkanoyl)xylostatin or 6′-N-alkyl-1-N-(α-hydroxy-ω-aminoalkanoyl)xylostatin; or $Z_1'$ is a 3″-O-(α-L-2‴,6‴-diaminodideoxyidopyranosyl)-β-D-ribofuranosyl group of which the hydroxyl and amino functions may be protected, and $Z_2'$ is a hydrogen atom or a known mono-valent hydroxyl-protecting group when the whole molecule of the compound of the formula (II) forms the 3′,4′-α-epoxy derivative of neomycin B, 6′-N-alkylneomycin B, 1-N-(α-hydroxy-ω-aminoalkanoyl)-neomycin B or 6′-N-alkyl-1-N-(α-hydroxy-ω-aminoalkanoyl)neomycin B; or $Z_1$ is a 3″-O-(α-L-2‴,6‴-diaminodideoxyglucopyranosyl)-β-D-ribofuranosyl group of which the hydroxyl and amino functions may be protected, and $Z_2$ is a hydrogen atom or a known mono-valent hydroxyl-protecting group when the whole molecule of the compound of the above formula (II) forms the 3′,4′-α-epoxy derivative of neomycin C, 6′-N-alkylneomycin C, 1-N-(α-hydroxy-ω-aminoalkanoyl)neomycin C or 6′-N-alkyl-1-N-(α-hydroxy-ω-aminoalkanoyl)neomycin C; or $Z_1'$ is a hydrogen atom and $Z_2'$ is a 3″-aminodeoxy-α-D-glucopyranosyl group of which the amino and hydroxyl functions may be protected when the whole molecule of the compound of the formula (II) forms the 3′,4′-α-epoxy derivative of kanamycin B, 6′-N-alkylkanamycin B, 1-N-(α-hydroxy-ω-aminoalkanoyl)kanamycin B or 6′-N-alkyl-1-N-(α-hydroxy-ω-aminoalkanoyl)kanamycin B.

When the starting 3′-O-sulfonyl compound of the formula (I) contains a hydroxyl-protecting group of the acyl type such as acetyl or benzoyl for the value of the group $Z_2$ and/or for blocking any hydroxyl group present in a glycosyl value of the group $Z_1$, such acyl type of the hydroxyl-protecting group can be removed (and thus, the acyl value of the group $Z_2$ is converted into a hydrogen atom, for instance) upon the conversion (i.e. the epoxidation) of said 3′-O-sulfonyl compound (I) into said 3′,4′-α-epoxyneamine derivative (II), because the deacylation takes place owing to the alkaline reaction conditions involved in the epoxidation in such a way that the deacylation reaction proceeds or occurs concurrently with the epoxidation reaction.

In carrying out the process of this invention the starting aminoglycosidic antibiotic derivative containing the 3′-O-sulfonylneamine moiety in its molecule, particularly the 3′-O-sulfonyl compound of the aforesaid formula (I), should be subjected to the epoxidation by treating it with an alkali at a temperature of up to 50° C in a reaction medium consisting of an inert solvent for a time sufficient to give a desired product. An alkali available for this purpose may be an alkali metal alkoxide, for example, an alkali metal lower alkoxide containing an alkyl group of 1–4 carbon atoms such as sodium methoxide, sodium ethoxide, potassium methoxide and potassium ethoxide; an alkali metal hydroxide such as sodium hydroxide and potassium hydroxide; an alkaline earth metal alkoxide; and an alkaline earth metal hydroxide such as calcium hydroxide and magnesium hydroxide. The solvent which is employed as the reaction medium in the present process should be inert to the reagents used and the reaction products as formed and may be water, a lower alkanol such as methanol, ethanol, propanol and butanol; diglyme, sulfolane, tetrahydrofuran, dimethylsulfoxide or a mixture of them. The process of this invention may preferably be conducted in such a manner that the starting 3′-O-sulfonyl compound is dissolved in a volume of a lower alkanol such as methanol and ethanol, the resulting alcoholic solution is admixed with a concentrated solution of sodium methoxide in methanol to a concentration of 1–5% by weight of sodium methoxide in the reaction mixture, the reaction mixture is agitated at ambient temperature for a period of 0.5 to 3 hours, the reaction mixture is then admixed with a volume of water to precipitate the reaction product comprising the 3′,4′-α-epoxy compound which is subsequently removed by filtration, washed with water and then dried.

If the resulting 3′,4′-α-epoxidation product, particularly the 3′,4′-α-epoxyneamine derivative of the formula (II), contains still the residual amino-protecting group and/or the hydroxyl-protecting group, these residual protective groups may be removed in a conventional manner, if required. Suitable methods for removing the residual protective groups are described, for example, in the aforesaid Belgian Pat. No. 808,393 and DT-OS No. 2,361,159 and may be chosen by the skilled in the art, depending on the nature of the protective groups remaining in the 3′,4′-α-epoxidation product.

Upon the removal of the protecting groups, care is to be made to avoid such reaction conditions which would result in the fission of the 3′,4′-α-epoxy ring. The 3′,4′-α-epoxidation product as obtained by the process of this invention may conveniently be purified chromatographically using a weak cation-exchange resin such as Amberlite CG 50.

Moreover, when the preparation of the starting 3′-O-sulfonyl derivative is made by selective 3′-O-sulfonylation of the parent aminoglycosidic antibiotic, it is usually required that the amino and hydroxyl functions of the parent aminoglycosidic antibiotic should partly or wholly be blocked with a known amino-protecting group and a known hydroxyl-protecting group prior to the 3'-O-sulfonylation. Suitable amino-protecting groups and hydroxyl-protecting groups for this purpose, as well as suitable methods for introduction of these protective groups into the initial, parent aminoglycosidic antibiotic may obviously be chosen by the skilled in the art, depending on the nature of the protective groups to be employed. For instance, there may be used such amino-protecting groups and hydroxyl-protecting groups and such methods of introducing these protective groups as detailed in the Belgian Pat. No. 808,393, DT-OS No. 2,350,169 and DT-OS No. 2,361,159.

The 3',4'-α-epoxyneamine derivative which is prepared according to the process of this invention is valuable, as it may be converted into a corresponding therapeutically useful 3'-deoxy derivative of aminoglycosidic antibiotic (see the Belgian Pat. No. 808,393; DT-OS No. 2,350,169 and DT-OS No. 2,361,159) by catalytic hydrogenation with hydrogen in the presence of a Raney nickel catalyst. Furthermore the 3',4'-α-epoxyneamine derivative obtained by the process of this invention may be converted into a corresponding 3'-epi-4'-deoxyneamine derivative by treating it with sodium borohydride, the 3'-epi-4'-deoxyneamine derivative being useful as semi-synthetic aminoglycosidic antibiotic derivative.

With such a cycloaliphatic compound containing two adjacent hydroxyl groups which are lying in a trans-relationship to each other and one hydroxyl group of which has been O-sulfonylated and the other of which is either in the free state or has been O-acetylated, it is known that such a cycloaliphatic compound may be converted into the corresponding epoxy derivative by treating with an alkali and thereby bringing about the interaction between the free or acetylated hydroxyl group and the carbon atom to which the O-sulfonylated hydroxyl group is attached, so that the epoxy group is formed therebetween, and that the epoxy derivative so produced bears said epoxy ring at one side which is opposite to the side where the O-sulfonylated hydroxyl group was initially positioned (see, for example, Anderson, J. M. and E. E. Percival's article in the "J.C.S." 1956, p. 819; Baker, B. R., R. E. Schaub and J. H. Williams' article in the "J.A.C.S." 77, p. 7 (1955); Peat, S. and L. F. Wiggins' article in the "J.C.S." 1938, p. 1088; Muller's article in the "Ber." 67, p. 421 (1934) and "Ber." 68, p. 1094 (1935); and Andre Rovowsky's "Heterocyclic Compounds" 2, Part I, pp. 1–529). However, the epoxidation reaction of this type has not ever been applied, neither scientifically nor commercially, in the field of amino-sugar compounds and particularly to the 3'-O-sulfonyl derivative of aminoglycosidic antibiotics for the purpose of producing a corresponding 3',4'-α-epoxy derivative therefrom.

This invention is now illustrated with reference to the following Examples to which this invention is not limited in any way.

EXAMPLE 1

Production of a 3',4'-α-epoxykanamycin B Derivative

A crude 2''-O-benzoyl-penta-N-ethoxycarbonyl-4'',6''-O-cyclohexylidene-3'-O-tosylkanamycin B (1500 mg; 70% purity and which was prepared as described in Example 1 of the Belgian Pat. No. 808,393 or DT-OS No. 2,361,159) was dissolved in 15 ml of a solution of 2.8% by weight of sodium methoxide in methanol. The resultant solution was agitated for 1 hour at ambient temperature to effect the epoxidation reaction and concurrent removal of the 2''-O-benzoyl group. To the reaction mixture was added a volume of water under stirring, and a colorless precipitate comprising penta-N-ethoxycarbonyl-4'',6''-O-cyclohexylidene-3',4'-α-epoxykanamycin B formed was removed by filtration. Yield 904 mg.

The precipitate was purified by subjecting it to a column chromatography on silica gel using ethyl acetateethanol (30:1 by volume) as the development solvent. Pure penta-N-ethoxycarbonyl-4'',6''-O-cyclohexylidene-3',4'-α-epoxykanamycin B (538 mg) was afforded. Yield 66%. m.p. 213°–216° C. $[\alpha]_D$ +64° (c 1.0, methanol).

Elemental Analysis: Found: C 50.40, H 6.76, N 7.37%; Calculated for $C_{39}H_{63}N_5O_{19}$: C51.71, H 7.01, N 7.73%.

EXAMPLE 2 (REFERENCE)

Production of 3'-epi-4'-deoxykanamycin B

Penta-N-ethoxycarbonyl-4'',6''-O-cyclohexylidene-3',4'-α-epoxykanamycin B (538 mg) obtained in Example 1 was admixed with 175 mg of sodium borohydride in 3.7 ml of diglyme, and the resulting admixture was heated for 1 hour on a water bath at 65° C under stirring.

After the heating was ended, the reaction mixture containing penta-N-ethoxycarbonyl-4'',6''-O-cyclohexylidene-3'-epi-4'-deoxykanamycin B which formed was extracted with ethyl acetate. The extract in ethyl acetate was concentrated to dryness, and the solid residue was heated for 50 minutes together with 38 ml of an aqueous solution of 60% acetic acid under reflux to effect the removal of the cyclohexylidene group. The reaction mixture was concentrated to dryness and the resulting solid residue comprising the decyclohexylidenated product was then admixed with 9.1 g of barium hydroxide and 12.5 ml of water. The admixture so obtained was heated for 17 hours under reflux to effect the removal of the ethoxycarbonyl group. The reaction mixture was neutralized by passage of gaseous carbon dioxide therethrough, and the barium carbonate precipitate formed was filtered off. The filtrate was passed through a column of 29 ml of a cation-exchange resin Amberlite CT 50 Type I ($NH_4^+$ form). The resin column was washed with a 10-fold volume of water and a 10-fold volume of 0.1 N aqueous ammonia and was subsequently eluted gradiently with 0.2 N to 0.35 N aqueous ammonia. The eluate was collected in 5 ml fractions, and the fraction Nos. 50 to 60 were combined together and concentrated to dryness under reduced pressure to give 139 mg of a crude 3'-epi-4'-deoxykanamycin B. This product was then subjected to a chromatographic purification in a column of 7 g of silica gel using n-butanolethanol-chloroform-17% aqueous ammonia (4:5:2:5 by volume) as the development solvent. Pure 3'-epi-4'-deoxykanamycin B (86 mg) was afforded as a colorless powder, mp. 167° C (dec.). Yield 13.9%. $[\alpha]_D$ +114.8° (c 1.0, $H_2O$).

3'-epi-4'-deoxykanamycin B showed a minimum inhibitory concentration of 3.12 to 6.25 mcg/ml against the growth of Staphylococcus aureus 209P Escherichia coli NIHJ, Escherichia coli K-12, and Pseudomonas aeruginosa A3, No. 12 and TI-13 strains.

EXAMPLE 3

Production of a 3',4'-α-epoxyribostamycin Derivative

5",6-di-O-acetyl-tetra-N-ethoxycarbonyl-2",3"-O-cyclohexylidene-3'-O-tosylribostamycin (459 mg), which is described as 5",6-di-O-acetyl-tetra-N-ethoxycarbonyl 2",3"-O-cyclohexylidene-3'-O-tosylvistamycin in Example 7 of the Belgian Pat. No. 808,393 or DT-OS No. 2,361,159) was dissolved in 4.5 ml of methanol, and to the resulting methanolic solution was added 0.5 ml of a solution of 28% sodium methoxide in methanol at ambient temperature under gentle agitation. The mixture was agitated for 1 hour at ambient temperature to effect the epoxidation and concurrent removal of the acetyl groups. The reaction mixture was then admixed with 50 ml of water and 101 mg of the colorless precipitate comprising tetra-N-ethoxycarbonyl-2",3"-O-cyclohexylidene-3',4'-α-epoxyribostamycin formed was collected by filtration. This precipitate was washed with water and the washing liquor was admixed with the mother liquor from which said precipitate was filtered off. The admixture so obtained (about 80 ml) was extracted four times with 50 ml portions of ethyl acetate, and the ethyl acetate extracts were combined together and washed twice with 30 ml portions of water. The washed extract was dried over anhydrous sodium sulfate overnight and was then concentrated to dryness under reduced pressure to give 237 mg of tetra-N-ethoxycarbonyl-2",3"-O-cyclohexylidene-3',4'-α-epoxyribostamycin as a second crop. The precipitate (101 mg) earlier obtained as a first crop was confirmed to be a substantially pure tetra-N-ethoxycarbonyl-2",3"-O-cyclohexylidene-3',4'-α-epoxyribostamycin which gave a single spot at an Rf value of about 0.54 on a silica gel thin layer chromatogram using ethyl acetate-ethanol (20:1 by volume) as the development solvent and detecting with sulfuric acid. The second crop (237 mg) of tetra-N-ethoxycarbonyl-2",3"-O-cyclohexylidene-3',4'-α-epoxyribostamycin gave a single spot at the same Rf value on the same silica gel thin layer chromatogram as mentioned above. Total yield 95%. This substance showed a softening point of 91° C and gradually melted up to 141° C.

Elemental analysis: Found: C 51.60, H 6.90, N 7.12%; Calculated for $C_{35}H_{56}N_4O_{17}$: C 52.23, H 6.96, N 6.96%.

EXAMPLE 4

Synthesis of a 3',4'-α-epoxyneamine Derivative

Tetra-N-ethoxycarbonyl-5,6-O-cyclohexylidene-3'-O-tosylneamine (600 mg, described in Example 5 of the Belgian Pat. No. 808,393 or DT-OS No. 2,361,159) was dissolved in 45 ml of ethanol, and the resulting solution was admixed with a solution of 28% sodium methylate in methanol. The admixture so obtained was allowed to stand for 30 minutes at ambient temperature to effect the epoxidation. The reaction mixture was admixed with 500 ml of water, and a white precipitate deposited was filtered off from said reaction mixture. This precipitate was washed with water and dried to give 460 mg of tetra-N:ethoxycarbonyl-5,6-O-cyclohexylidene-3',4'-α-epoxyneamine.

EXAMPLE 5

Synthesis of 3',4'-α-epoxykanamycin B (a) 2"-O-benzoyl-penta-N-benzyloxycarbonyl-4", 6"-O-cyclohexylidene-3'-O-tosylkanamycin B (407 mg) [which was prepared from 2"-O-benzoyl-3',4'; 4",6"-di-O-cyclohexylidene-penta-N-salicylidenekanamycin B described in Example 1(a) (iii) of the Belgian Pat. No. 808,393 or DT-OS No. 2,361,159 by subjecting the latter kanamycin B derivative to the process of Example 1(a) (iv) using benzyl chloroformate in place of ethoxycarbonyl chloride, followed by sulfonylating with tosyl chloride in a similar manner to Example 1(b) of said Belgian Pat. or DT-OS] was dissolved in a mixture of 12 ml of dioxane, 17 ml of water and 2 ml of acetic acid. The resulting solution was subjected to catalytic reduction with hydrogen gas at atmospheric pressure and at ambient temperature for 6 hours in the presence of an amount of palladium-black catalyst added thereto, whereby the removal of the benzyloxycarbonyl group was effected. The reaction mixture so obtained was filtered to remove the palladium catalyst, and the filtrate was concentrated. The concentrated filtrate containing 2"-O-benzoyl-4",6"-O-cyclohexylidene-3'-O-tosylkanamycin B acetate was admixed with 15 ml of aqueous 80% acetic acid and the admixture was heated at 65° C for 3 hours, whereby the removal of the cyclohexylidene group was effected. The reaction mixture so obtained was neutralized by addition of an amount of sodium methylate and then concentrated to a smaller volume. The concentrated residue was taken up into 8 ml of methanol and admixed with 0.8 ml of a solution of 28% sodium methylate in methanol. The resulting admixture was allowed to stand for 1 hour at ambient temperature to effect the epoxidation and concurrent removal of the 2"-O-benzoyl group. From the reaction mixture so obtained was taken a portion thereof as a sample. Analysis of this sample showed that 3',4'-α-epoxykanamycin B was present in said reaction mixture.

(b) The reaction mixture was neutralized by the addition of acetic acid and then passed through a column of 4 ml of Amberlite CG 50 ($NH_4^+$ form) to make the 3',4'-α-epoxykanamycin B product by the cation-exchange resin. The resin column was eluted with 0.15 N to 0.35 N aqueous ammonia and the eluate was collected in 1 ml fractions. The combined fraction Nos. 20 to 25 was concentrated to dryness to obtain 3',4'-α-epoxykanamycin B. Yield 15%.

EXAMPLE 6

Synthesis of a 3',4'-α-epoxy-6'-N-methylkanamycin B Derivative

2"-O-benzoyl-penta-N-ethoxycarbonyl-4",6"-O-cyclohexylidene-3'-O-tosyl-6'-N-methylkanamycin B (1.0 g) [which was obtained by reacting 1.2 g of 6'-N-methylkanamycin B (described in the "Journal of Antibiotics" Vol. 25, No. 12, pages 743–745, December, 1972 and in Japanese patent application pre-publication No. 41345/74 published on Apr. 18, 1974) successively with salicylaldehyde, 1.1-dimethoxycyclohexane, benzoyl chloride, aqueous acetic acid, ethoxycarbonyl chloride and tosyl chloride in the same manner as described in Example 1(a), (b) of the Belgian Pat. No. 808,393 or DT-OS No. 2,361,159] was dissolved in 50 ml of ethanol, and the resulting solution was admixed with 5 ml of a solution of 28% sodium methylate in methanol. The admixture so obtained was allowed to stand for 1 hour at ambient temperature to effect the epoxidation and concurrent removal of the 2"-O-benzoyl group. A portion was taken out as a sample from the reaction mixture and analyzed, and it was then observed that the reaction mixture contained penta-N-ethoxycarbonyl-4",6"-O-cyclohexylidene-3',4'-α-epoxy-6'-N-methylkanamycin B.

What we claim is:

1. 3'-epi-4'-deoxykanamycin B.

* * * * *